(12) United States Patent
Ko et al.

(10) Patent No.: US 9,956,255 B1
(45) Date of Patent: May 1, 2018

(54) **METHOD TO REDUCE BODY WEIGHT, FAT ACCUMULATION AND ADIPOCYTE SIZE USING *PARABACTEROIDES GOLDSTEINII***

(71) Applicant: Chang Gung Biotechnology Corp., Taipei (TW)

(72) Inventors: Yun-Fei Ko, Taipei (TW); Jan Martel, Taipei (TW); Tsung-Ru Wu, Taipei (TW); Chih-Jung Chang, Taipei (TW); Chuan-Sheng Lin, Taipei (TW); Jian-Ching Liau, Taipei (TW); Wei-Chang Wang, Taipei (TW); Chen-Yaw Chiu, Taipei (TW); Chia-Chen Lu, Taipei (TW); David Marcelo Ojcius, Taipei (TW); Hsin-Chih Lai, Taipei (TW); John D. Young, Taipei (TW)

(73) Assignee: CHANG GUNG BIOTECHNOLOGY CORP., Taipei (TW)

( * ) Notice: Subject to any disclaimer, the term of this patent is extended or adjusted under 35 U.S.C. 154(b) by 0 days. days.

(21) Appl. No.: 15/728,165

(22) Filed: Oct. 9, 2017

(30) Foreign Application Priority Data

Aug. 18, 2017 (TW) .............................. 106128174 A

(51) Int. Cl.
A61K 49/00 (2006.01)
A01N 63/00 (2006.01)
A01N 65/00 (2009.01)
A61K 35/741 (2015.01)
A61K 9/00 (2006.01)

(52) U.S. Cl.
CPC .......... *A61K 35/741* (2013.01); *A61K 9/0053* (2013.01)

(58) Field of Classification Search
CPC .... A61K 35/00; A61K 35/741; A61K 35/742; A61K 35/744
USPC ................................. 424/9.1, 9.2, 93.1, 93.4
See application file for complete search history.

*Primary Examiner* — Rodney P Swartz
(74) *Attorney, Agent, or Firm* — WPAT, PC

(57) ABSTRACT

The present invention describes a method to reduce body weight, fat accumulation and adipocyte size by administering the probiotic bacterium *Parabacteroides goldsteinii*. This probiotic bacterium can therefore be used to treat obesity in animals and humans.

9 Claims, 13 Drawing Sheets

METHOD TO REDUCE BODY WEIGHT, FAT ACCUMULATION AND ADIPOCYTE SIZE USING *PARABACTEROIDES GOLDSTEINII*

CROSS-REFERENCE TO RELATED APPLICATION

This application claims priority of Taiwan patent application No. 106128174, filed on Aug. 18, 2017, the content of which is incorporated herein in its entirety by reference.

BACKGROUND OF THE INVENTION

1. Field of the Invention

The present invention comprises a method to reduce body weight, fat accumulation and adipocyte size in overweight subjects by administering the probiotic bacterium *Parabacteroides goldsteinii*. This bacterium can therefore be used to treat obesity.

2. The Prior Art

The incidence of obesity has increased in recent years, reaching worldwide epidemic status. In 2014, the World Health Organization estimated that 39% of the human population was overweight (1.9 billion people), and that 13% was obese (600 million people). Obese individuals show increased risk of developing several health problems, including hypertension, cardiovascular disease, osteoarthritis, type 2 diabetes mellitus and cancer. Accordingly, obesity reduces quality of life and may lead to premature death. While genes may be involved in the development of obesity, the obesity epidemic has been mainly attributed to high-calorie diets and sedentary lifestyle. Obesity and its complications are therefore preventable by lifestyle changes.

Although low-calorie diets and regular exercise are used to reduce body weight and treat obesity, these approaches are difficult to implement and their efficacy has been limited, mainly due to adaptive physiological mechanisms that maintain energy stores in the body. Pharmaceutical drugs have been approved for long-term obesity treatment (e.g., orlistat, phentermine/topiramate), but these are often associated with serious side-effects which limit treatment efficacy and patient compliance. Weight-loss surgery leads to considerable weight loss, but this intervention is not suitable for all overweight individuals. For these reasons, alternative strategies to reduce body weight and fat accumulation in a safe and effective manner would be highly beneficial.

SUMMARY OF THE INVENTION

A primary objective of the present invention is to provide a method for reducing body weight, fat accumulation and adipocyte size, comprising administering a composition comprising an effective amount of *Parabacteroides goldsteinii* bacterium to a subject in need thereof.

According to an embodiment of the present invention, *P. goldsteinii* is a live bacterium.

According to an embodiment of the present invention, the effective amount of *P. goldsteinii* bacterium is between 0.001 CFUs/kg to $5 \times 10^{18}$ CFUs/kg of body weight per day, and the effective amount of *P. goldsteinii* bacterium is $6.1 \times 10^9$ CFUs/individual per day.

According to an embodiment of the present invention, the composition comprises additional active ingredient, and the active ingredient is at least one selected from the group consisting of protein, monosaccharide, disaccharide, oligosaccharide, polysaccharide, carbohydrate, amino acid, lipid, vitamin and combinations thereof.

According to an embodiment of the present invention, the composition comprises other bacteria.

According to an embodiment of the present invention, the composition is in the form of a solution, gelatin capsule, softgel capsule and pressed tablet.

According to an embodiment of the present invention, the composition is orally administered to the subject in need thereof.

Accordingly, the present invention provides a method for treating obesity by using *P. goldsteinii*; the bacterium can reduce body weight, fat accumulation and adipocyte size to reach the purpose of preventing and treating obesity. Therefore, the method of the present invention provides a new strategy to prevent and treat obesity.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
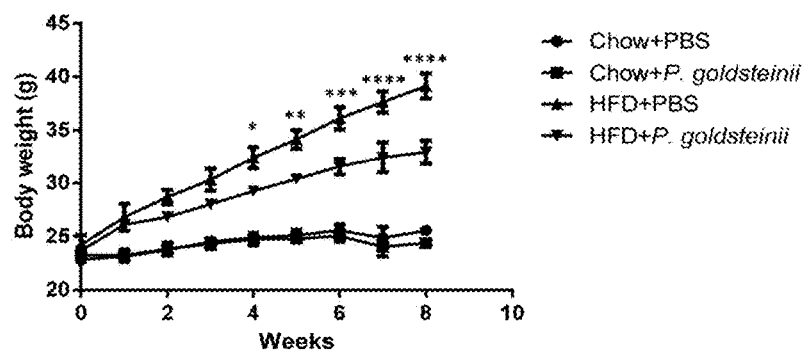
FIG. 1 shows that *P. goldsteinii* supplementation reduces body weight in mouse fed with a high-fat diet (HFD). The animal groups consist of mice fed with standard chow and treated with phosphate buffered saline (PBS) (Chow+PBS); mice fed with standard chow and treated with *P. goldsteinii* (Chow+*P. goldsteinii*); mice fed with HFD and treated with PBS (HFD+PBS); and mice fed with HFD and treated with *P. goldsteinii* (H1-D+*P. goldsteinii*). The data shown represent means±standard error of the mean (SEM). Body weight differences were analyzed using the two-way ANOVA Bonferroni post hoc test (*, $P<0.05$; , $P<0.01$; *, $P<0.001$; ****, $P<0.0001$; HFD+*P. goldsteinii* vs. HFD+PBS).

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

The "effective amount" described in the present invention represents the amount of bacteria that can reduce body weight, fat accumulation and adipocyte size in animals and humans. The effective amount may vary depending on the organism or individual treated but can be determined experimentally using various techniques, including a dose escalation study.

As used herein, the data provided represent experimental values that can vary within a range of ±20%, preferably within ±10%, and most preferably within ±5%.

The present invention provides a method for reducing body weight, fat accumulation and adipocyte size, comprising administering a composition comprising an effective amount of *Parabacteroides goldsteinii* bacterium to a subject in need thereof. The experiments below show the effects of *P. goldsteinii* on body weight, epididymal and subcutaneous fat accumulation, adipocyte size, mean energy intake and blood biochemistry markers. Generally, *P. goldsteinii* bacterium can be given to mammals and humans at a dose ranging from 0.001 CFUs/kg to $5 \times 10^{18}$ CFUs/kg per day. The invention is described in detail below.

In the present invention, live *P. goldsteinii* bacterium can effectively treat obesity and reduce body weight, fat accumulation and adipocyte size. The *P. goldsteinii* bacterium of the present invention can be added to the diet of a subject in need thereof, as a drug, a beverage, a daily supplement, or a food, without incurring in significant lifestyle changes, toxicity or other unfavorable health conditions.

In the present invention, eight-week old C57BL/6Narl mice are fed with standard chow (13.5% of energy from fat; LabDiet 5001; LabDiet, USA) in the control group or with high-fat diet (HFD) (60% of energy from fat; TestDiet 58Y1; TestDiet, USA) in the experimental group. The mice are also treated daily with 200 μL of *P. goldsteinii* ATCC strain BAA-1180 ($2 \times 10^6$ CFUs), *P. merdae* ATCC strain 43184 ($2 \times 10^6$ CFUs), or PBS daily for 8 weeks by intragastric gavage (n=5 mice per group). The animal groups consist of (1) mice fed with standard chow and treated with PBS (Chow+PBS); (2) mice fed with standard chow and treated with *P. goldsteinii* (Chow+*P. goldsteinii*); (3) mice fed with HFD and treated with PBS (HFD+PBS); (4) mice fed with HFD and treated with *P. goldsteinii* (HFD+*P. goldsteinii*); and (5) mice fed with HFD and treated with *P. merdae* (HFD+*P. merdae*).

Example 1

Figure 2:
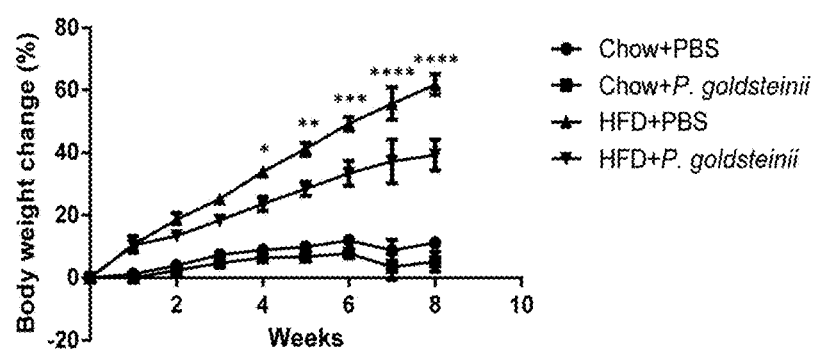
FIG. 2 shows that *P. goldsteinii* supplementation reduces relative body weight change in HFD-fed mice. Animal treatment and statistical analysis were performed as in FIG. 1 (*, $P<0.05$; , $P<0.01$; *, $P<0.001$; ****, $P<0.0001$; HFD+*P. goldsteinii* vs. HFD+PBS).
Figure 3:
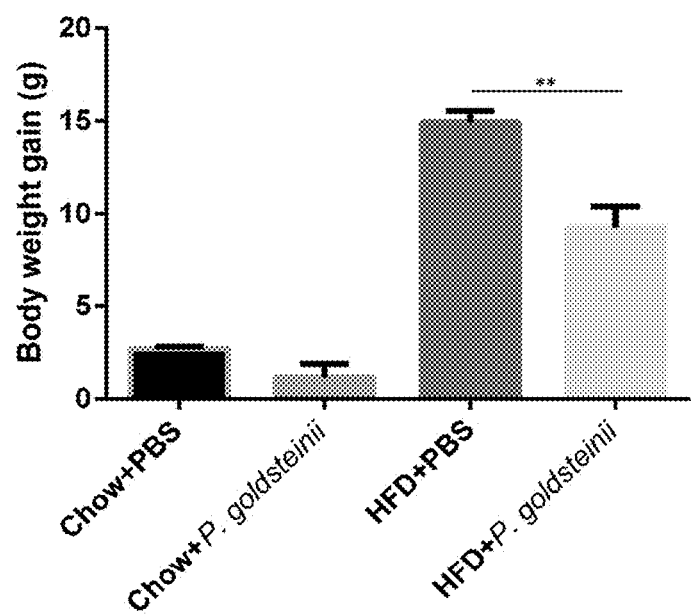
FIG. 3 shows the effects of *P. goldsteinii* supplementation on body weight gain in HFD-fed mice. Mice were treated for 8 weeks as in FIG. 1. Data are expressed as means±SEM. Body weight differences were analyzed using one-way Bonferroni's post hoc ANOVA test (**, $P<0.01$; HFD+*P. goldsteinii* vs. HFD+PBS).
Figure 4:
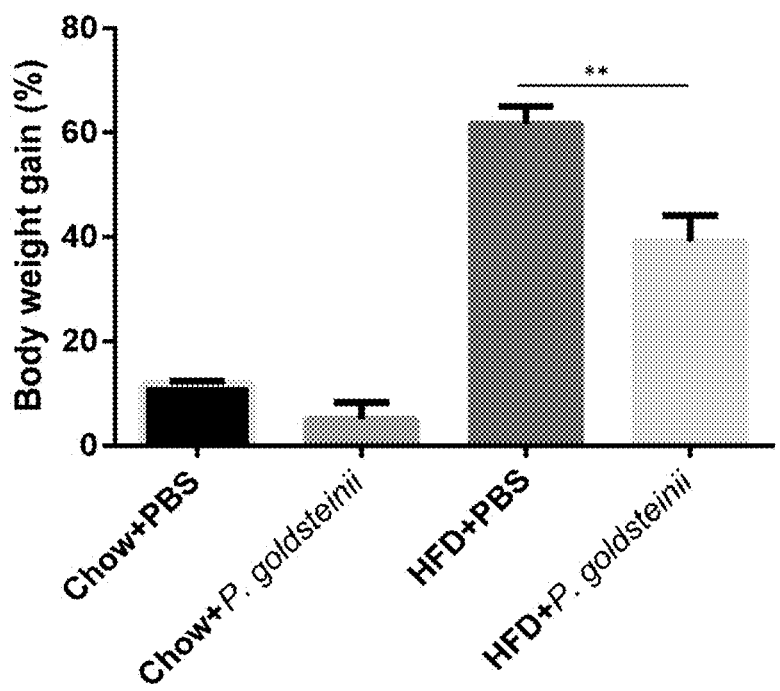
FIG. 4 shows that *P. goldsteinii* supplementation reduces relative body weight gain in HFD-fed mice. Mice were treated for 8 weeks as in FIG. 1. Statistical analysis was done using one-way Bonferroni's post hoc ANOVA test (**, $P<0.01$; HFD+*P. goldsteinii* vs. HFD+PBS).
Figure 5:
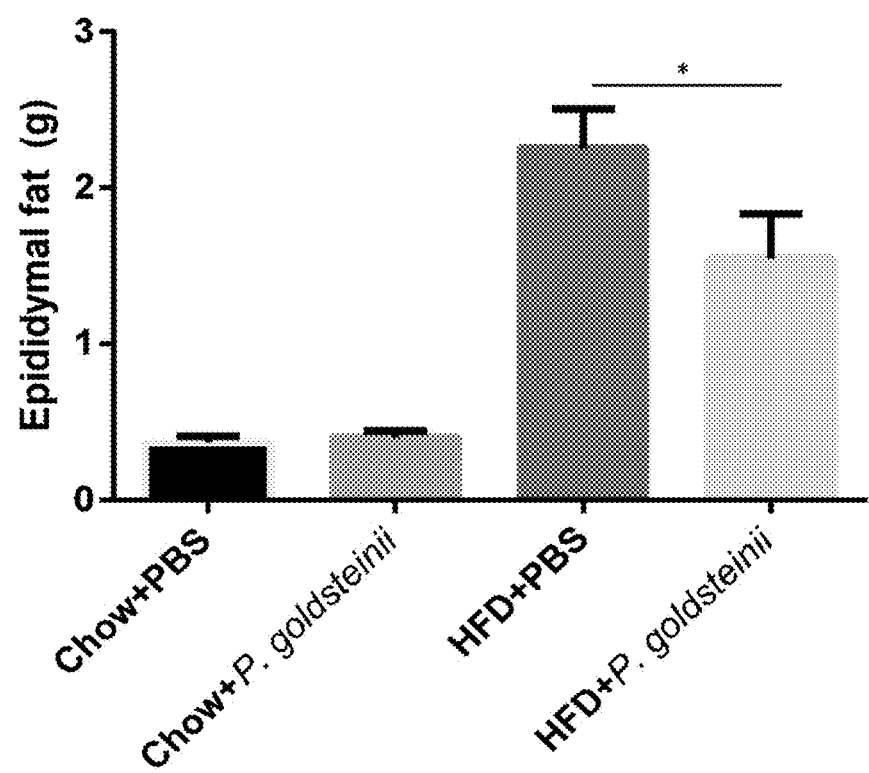
FIG. 5 shows reduction of epididymal fat following *P. goldsteinii* supplementation in HFD-fed mice. Mice were treated for 8 weeks as in FIG. 1. Statistical analysis was performed using one-way Bonferroni's post hoc ANOVA test (*, $P<0.05$; HFD+*P. goldsteinii* vs. HFD+PBS).
Figure 6:
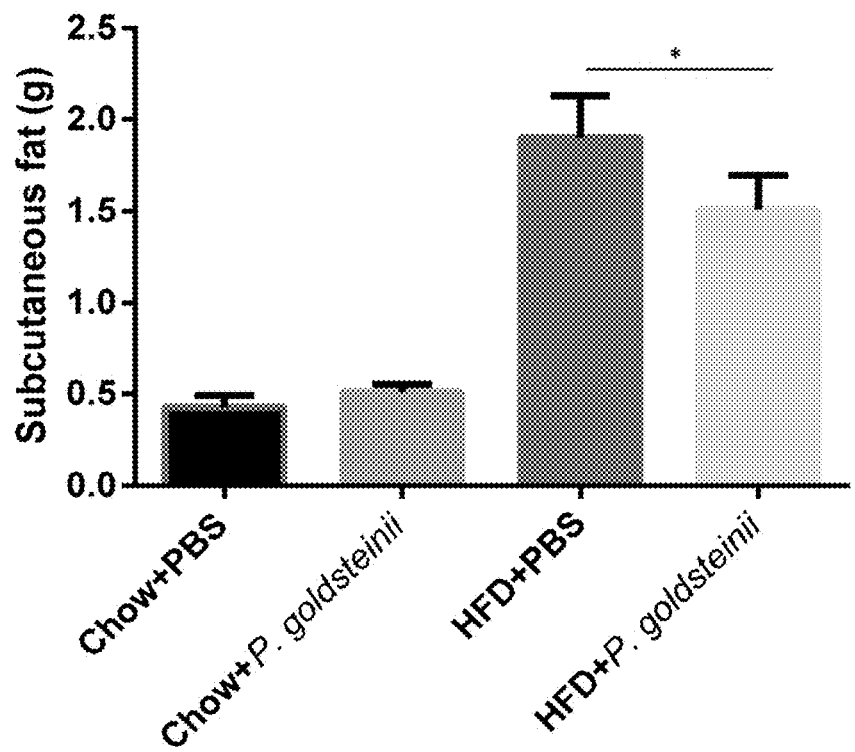
FIG. 6 shows reduction of subcutaneous fat following *P. goldsteinii* supplementation in HFD-fed mice. Mice were treated for 8 weeks as in FIG. 1. Statistical analysis was performed using one-way Bonferroni's post hoc ANOVA test (*, $P<0.05$; HFD+*P. goldsteinii* vs. HFD+PBS).
Figure 7A:
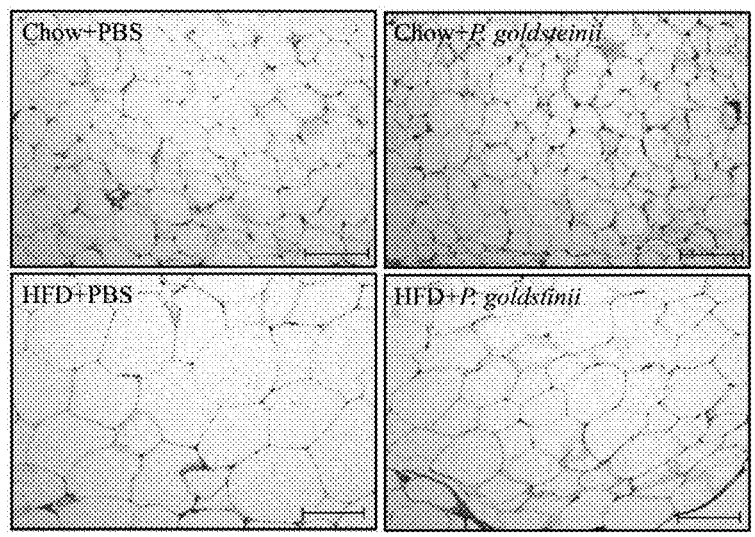
FIG. 7A shows the effects of *P. goldsteinii* supplementation on epididymal fat tissues in HFD-fed mice. Mice were treated for 8 weeks as in FIG. 1. Tissues were stained with hematoxylin and eosin (H&E). Scale bars, 50 μm.
Figure 7B:
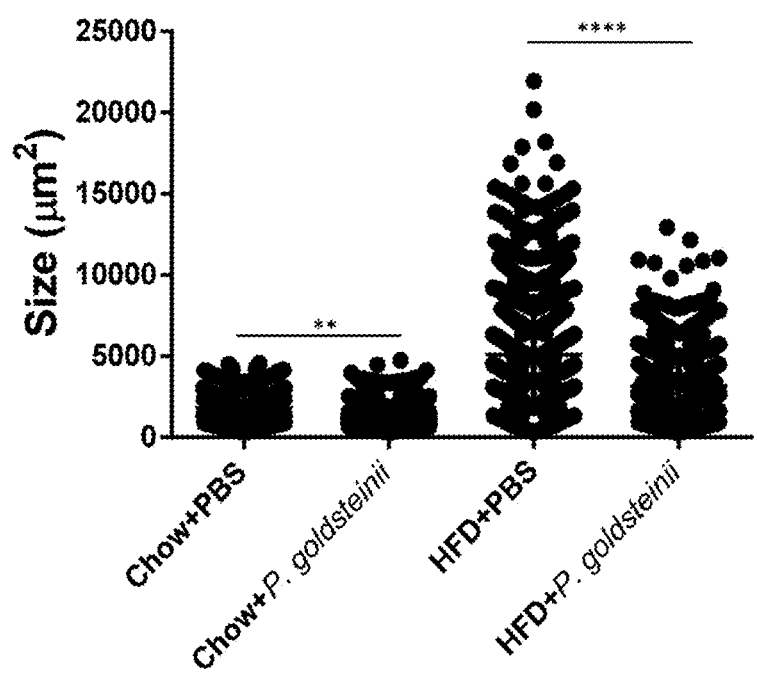
FIG. 7B shows reduction of epididymal adipocyte size following *P. goldsteinii* supplementation in HFD-fed mice. Mice were treated for 8 weeks as in FIG. 1. Statistical analysis was performed using one-way Bonferroni's post hoc ANOVA test (****, P<0.0001; HFD+*P. goldsteinii* vs. HFD+PBS).

Effects of *P. goldsteinii* Bacterium on Body Weight, Fat Accumulation and Adipocyte Size in HFD-Fed Mice FIGS. 1-7 show the effects of *P. goldsteinii* of the present invention on the body weight, fat levels and adipocyte size of chow-fed and HFD-fed mice. Feeding with the HFD increased body weight, fat levels and adipocyte size compared to feeding with chow (FIGS. 1-7). Notably, mice treated with HFD+*P. goldsteinii* showed reduction of absolute and relative body weight (FIGS. 1 and 2), absolute and relative body weight gain (FIGS. 3 and 4), epididymal fat (FIG. 5), subcutaneous fat (FIG. 6) and adipocyte size (FIGS. 7A and 7B) compared with HFD-fed mice. Notably, *P. goldsteinii* supplementation reduced the body weight of HFD-fed mice by 6.2 g compared to the HFD group (FIG. 1), representing a reduction of 22.5% of body weight (FIG. 2).

As shown in FIGS. 1-7, *P. goldsteinii* can reduce body weight, fat accumulation and adipocyte size in HFD-fed mice. Based on these results, the effective amount of *P. goldsteinii* required to produce anti-obesity effects in mice with an average body weight of 23 g is $8.7 \times 10^7$ CFUs/kg per day for a period of 8 weeks. Accordingly, the effective amount of *P. goldsteinii* that would produce similar anti-obesity effects in a human subject with an average weight of 70 kg is estimated at $6.1\times10^9$ CFUs/individual per day.

Example 2

Figure 8:
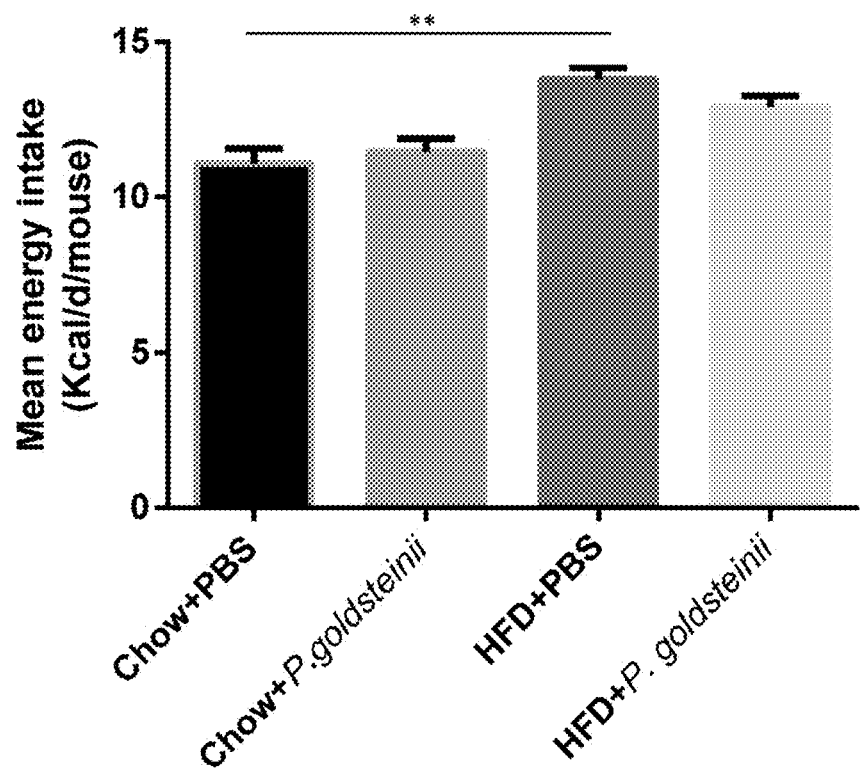
FIG. 8 shows the absence of effects of *P. goldsteinii* supplementation on daily energy intake in HFD-fed mice. Mice were treated for 8 weeks as in FIG. 1. Statistical analysis was performed using one-way Bonferroni's post hoc ANOVA test (**, P<0.01; Chow+PBS vs. HFD+PBS).
Figure 9:
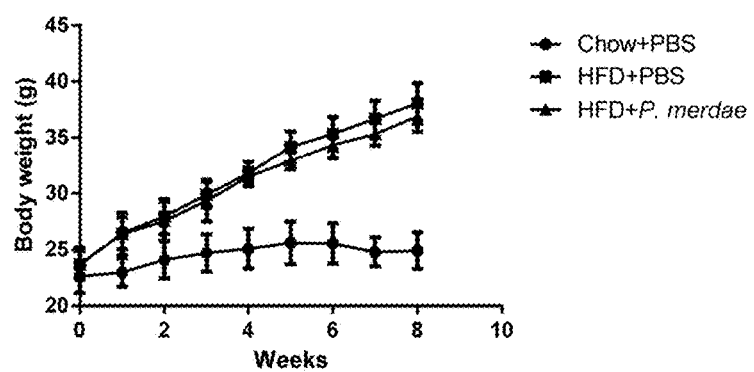
FIG. 9 shows that *Parabacteroides merdae* supplementation fails to reduce body weight in HFD-fed mice. The animal groups consist of mice fed with standard chow and treated with PBS (Chow+PBS); mice fed with HFD and treated with PBS (HFD+PBS); and mice fed with HFD and treated with *P. merdae* (H1-1)+*P. merdae*). The data shown represent means±SEM. After 8 weeks, the body weight of HFD+PBS mice did not differ from that of mice in the HFD+*P. merdae* group as analyzed using the two-way ANOVA Bonferroni post hoc test.
Figure 10:
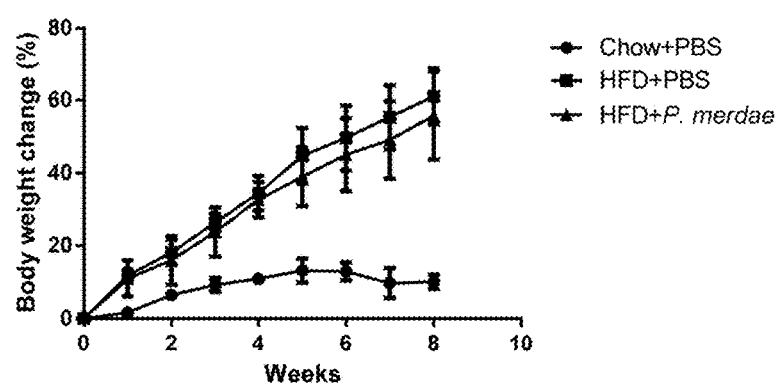
FIG. 10 shows that *P. merdae* fails to reduce relative body weight change in HFD-fed mice. Experiments and statistical analysis were performed as in FIG. 9. No statistically significant difference was noted between the body weight of HFD+PBS and HFD+*P. merdae* groups after 8 weeks.
Figure 11:
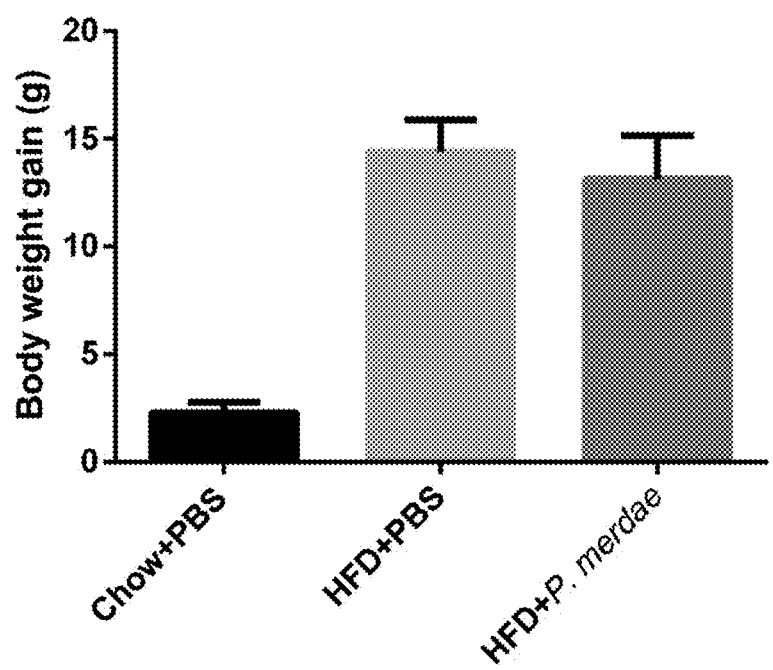
FIG. 11 shows that *P. merdae* fails to affect body weight gain in HFD-fed mice. Animal treatments were performed as in FIG. 9. After 8 weeks of feeding, the body weight of mice fed HFD+PBS did not differ from that of mice fed with HFD+*P. merdae*. Data were analyzed using the one-way ANOVA Bonferroni post hoc test.
Figure 12:
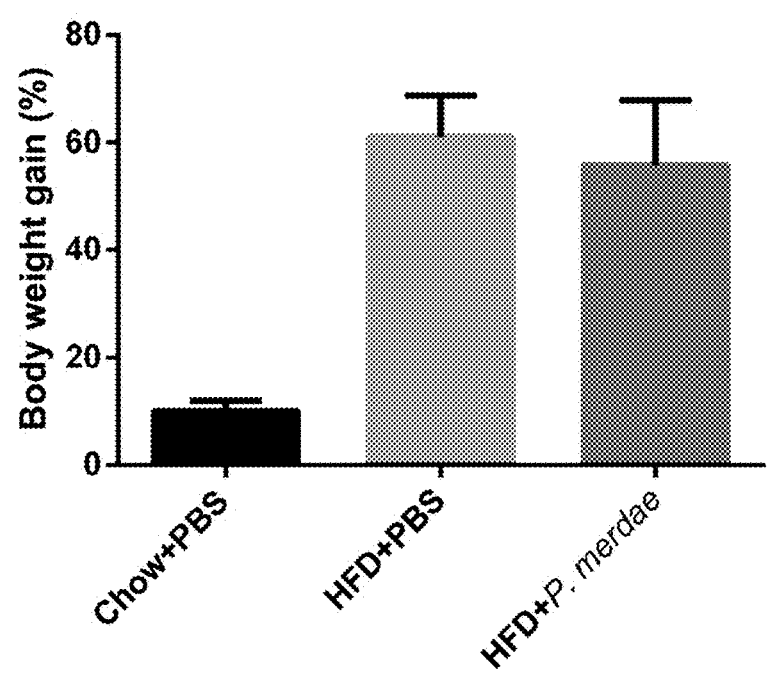
FIG. 12 shows that *P. merdae* does not affect relative body weight gain in HFD-fed mice. Experiments were performed as in FIG. 9. The body weight of mice fed HFD+PBS did not differ from that of mice fed with HFD+*P. merdae* after 8 weeks of feeding. Data were analyzed using the one-way ANOVA Bonferroni post hoc test.

Effects of *P. goldsteinii* Bacterium Treatment on Mean Energy Intake in HFD-Fed Mice FIG. 8 shows the effects of *P. goldsteinii* treatment on mean energy intake of chow-fed and HFD-fed mice. While the HFD-PBS group showed higher mean energy intake levels compared to the Chow+PBS and Chow+*P. goldsteinii* groups, the *P. goldsteinii* treatment group did not affect mean energy intake in HFD-fed mice. These results suggest that the *P. goldsteinii* treatment did not affect appetite.

Example 3

Effects of *P. goldsteinii* Bacterium Treatment on Blood Biochemical Parameters in Chow-Fed Mice The present invention discloses the absence of effects *P. goldsteinii* treatment on blood biochemical parameters in chow-fed mice. The blood biochemical parameters examined include those used to assess liver functions, such as the enzymes aspartate transaminase (AST) and alanine transaminase (ALT), as well as the blood biochemical parameters used to assess kidney functions, such as blood urea nitrogen (BUN) and creatinine. Blood biochemical parameters were monitored using a biochemical analyzer (Hitachi 7080, Hitachi, Japan). As shown in Table 1, no statistical differences were noted between the blood biochemical parameters of chow-fed mice treated with either PBS or *P. goldsteinii*, indicating that *P. goldsteinii* did not affect liver or kidney functions under these conditions.

TABLE 1

Effects of *P. goldsteinii* Bacterium Treatment on Blood Biochemical Parameters in Chow-Fed Mice
Analysis of liver and kidney functions in mice treated with *Parabacteroides goldsteinii*

|  | Chow + PBS | Chow + *P. goldsteinii* |
|---|---|---|
| Aspartate transaminase (AST; U/l) | 73.9 ± 13.4 | 72.4 ± 19.9 |
| Alanine transaminase (ALT; U/l) | 30.4 ± 11.2 | 26.3 ± 4.8 |
| Blood urea nitrogen (BUN; mg/dl) | 29.8 ± 3.8 | 28.3 ± 2.8 |
| Creatinine (mg/dl) | 0.20 ± 0.05 | 0.20 ± 0.04 |

No statistically significant differences were noted between the two groups. Experiments were performed in triplicate (n = 14-16 mice per group in total).

Comparable Example 1

Effects of Other *Parabacteroides* Bacterium Species on Body Weight and Body Weight Gain in HFD-Fed Mice The present invention discloses the effects of *P. merdae*, another species of the *Parabacteroides* genus which was used as a negative control, on the body weight of chow-fed and HFD-fed mice. After 8 weeks of feeding, *P. merdae* supplementation failed to reduce absolute body weight (FIG. 9), relative body weight change (FIG. 10), absolute body weight gain (FIG. 11) and relative body weight gain (FIG. 12) in HFD-fed mice. In other words, mice of the HFD+*P. merdae* group showed no statistically significant difference in the said body weight parameters compared with mice treated with HFD+PBS (FIGS. 9-12). These results indicate that the anti-obesity property of *P. goldsteinii* is not a general characteristic of the *Parabacteroides* genus but is limited to the species *P. goldsteinii*.

The present invention provides a method for treating obesity using the probiotic bacterium *P. goldsteinii*. The *P. goldsteinii* bacterium can reduce body weight, fat accumulation and adipocyte size in animals and humans. While many *Parabacteroides* species exist (e.g., *P. merdae*), the present invention discloses that not all *Parabacteroides* species produce anti-obesity effects in HFD-fed mice. Therefore, the present invention provides a new strategy to manage body weight, induce weight loss and reduce fat accumulation in humans. This strategy has obvious potential commercial applications given the vast amount of products and treatments available on the market to reduce body weight or maintain an optimal weight and general health.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for reducing body weight, fat accumulation and adipocyte size of a subject on a high fat diet, comprising administering a composition comprising an effective amount of *Parabacteroides goldsteinii* bacterium to said subject.

2. The method according to claim 1, wherein the *Parabacteroides goldsteinii* bacterium is a live bacterium.

3. The method according to claim 1, wherein the effective amount of the *Parabacteroides goldsteinii* bacterium is between 0.001 CFUs/kg to $5\times10^{18}$ CFUs/kg of body weight per day.

4. The method according to claim 1, wherein the effective amount of the *Parabacteroides goldsteinii* bacterium is $6.1\times10^9$ CFUs per day.

5. The method according to claim 1, wherein the composition further comprises an additional active ingredient.

6. The method according to claim 5, wherein the additional active ingredient is at least one selected from the group consisting of protein, monosaccharide, disaccharide, oligosaccharide, polysaccharide, carbohydrate, amino acid, lipid, vitamin and combinations thereof.

7. The method according to claim 1, wherein the composition further comprises other bacteria.

8. The method according to claim 1, wherein the composition is in the form of a solution, gelatin capsule, softgel capsule or pressed tablet.

9. The method according to claim 1, wherein the composition is orally administered to said subject.

* * * * *